(12) United States Patent
Lattner et al.

(10) Patent No.: US 8,461,397 B2
(45) Date of Patent: Jun. 11, 2013

(54) OXIDATION OF HYDROCARBONS (75) Inventors: James R. Lattner, Laporte, TX (US);
Mark Hagemeister, Houston, TX (US);
Jon E. R. Stanat, Westhampton Beach, NY (US); John S. Buchanan, Lambertville, NJ (US); Jihad M. Dakka, Whitehouse Station, NJ (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 6 days.

(21) Appl. No.: 13/060,805

(22) PCT Filed: Aug. 17, 2009

(86) PCT No.: PCT/US2009/054000
§ 371 (c)(1),
(2), (4) Date: Mar. 29, 2011

(87) PCT Pub. No.: WO2010/042273
PCT Pub. Date: Apr. 15, 2010

(65) Prior Publication Data
US 2011/0172466 A1 Jul. 14, 2011

Related U.S. Application Data (60) Provisional application No. 61/104,301, filed on Oct. 10, 2008.

(51) Int. Cl.
*C07C 409/02* (2006.01)

(52) U.S. Cl.
USPC .................. 568/573; 568/700; 568/338

(58) Field of Classification Search
USPC .................. 568/573, 338, 700; 549/239
See application file for complete search history.

(56) References Cited

U.S. PATENT DOCUMENTS

| | | | |
|---|---|---|---|
| 3,418,256 A | 12/1968 | Rigney et al. | |
| 3,959,381 A | 5/1976 | Arkell et al. | |
| 4,094,918 A | 6/1978 | Murtha et al. | |
| 4,122,125 A | 10/1978 | Murtha et al. | |
| 4,136,123 A | 1/1979 | Hutchings | |
| 4,177,165 A | 12/1979 | Murtha et al. | |
| 4,206,082 A | 6/1980 | Murtha et al. | |
| 4,255,592 A | 3/1981 | Kawai et al. | |
| 4,282,383 A | 8/1981 | Dai et al. | |
| 4,450,303 A | 5/1984 | Drake | |
| 5,030,739 A | 7/1991 | Foricher et al. | |
| 5,053,571 A | 10/1991 | Makkee | |
| 5,166,454 A | 11/1992 | Harandi et al. | |
| 5,298,667 A | 3/1994 | Iwanaga et al. | |
| 5,405,814 A | 4/1995 | Beech, Jr. et al. | |
| 5,981,420 A | 11/1999 | Nakano et al. | |
| 6,037,513 A | 3/2000 | Chang et al. | |
| 6,291,718 B1 | 9/2001 | Matsui et al. | |
| 6,720,462 B2 | 4/2004 | Kuhnle et al. | |
| 6,852,893 B2 | 2/2005 | Kuhnle et al. | |
| 7,038,089 B2 | 5/2006 | De Frutos Escrig et al. | |
| 7,326,815 B2 | 2/2008 | Dakka et al. | |
| 2002/0169331 A1 | 11/2002 | Miura et al. | |
| 2003/0083527 A1 | 5/2003 | Kuhnle et al. | |
| 2004/0162448 A1 | 8/2004 | Yang et al. | |
| 2004/0236152 A1 | 11/2004 | Black et al. | |
| 2005/0043559 A1 | 2/2005 | Marhold et al. | |
| 2005/0080289 A1* | 4/2005 | Murata et al. | 562/542 |
| 2005/0167658 A1 | 8/2005 | Williams et al. | |
| 2006/0036100 A1* | 2/2006 | Ishii et al. | 548/402 |
| 2006/0281629 A1* | 12/2006 | Ishii et al. | 502/167 |
| 2008/0171881 A1* | 7/2008 | Hirai et al. | 546/243 |
| 2008/0269507 A1* | 10/2008 | Kajikawa et al. | 549/239 |
| 2010/0179351 A1 | 7/2010 | Chen et al. | |

FOREIGN PATENT DOCUMENTS

| | | |
|---|---|---|
| DE | 2 300 903 | 1/1973 |
| EP | 1 074 536 | 2/2001 |
| EP | 1 088 807 | 4/2001 |
| EP | 1 088 809 | 4/2001 |
| JP | 62-114922 | 5/1987 |
| JP | 11-180913 | 7/1999 |
| JP | 2004-035460 | 2/2002 |
| JP | 2002-282698 | 10/2002 |
| WO | 94/20213 | 9/1994 |
| WO | 99/47485 | 9/1999 |
| WO | 2006/015826 | 2/2006 |
| WO | 2009/025939 | 2/2009 |
| WO | 2009/128984 | 10/2009 |
| WO | 2010/098916 | 9/2010 |
| WO | 2010/138248 | 12/2010 |

OTHER PUBLICATIONS

Chitwood et al; Industrial and Engineering Chemistry, 1952; 44 (7), 1696-1698.*

(Continued)

*Primary Examiner* — Johann R. Richter
*Assistant Examiner* — Pancham Bakshi
(74) *Attorney, Agent, or Firm* — Anthony G. Boone; Jamie L. Sullivan; Siwen Chen (57) ABSTRACT

In a process for oxidizing a hydrocarbon to the corresponding hydroperoxide, alcohol, ketone, carboxylic acid or dicarboxylic acid, a reaction medium comprising a hydrocarbon is contacted with an oxygen-containing gas in a reaction zone and in the presence of a catalyst comprising a cyclic imide. During the oxidation process, a portion of the reaction medium is continuously or intermittently removed from the reaction zone, is stripped of water and organic acid impurities and then returned to the reaction zone.

18 Claims, 3 Drawing Sheets

OTHER PUBLICATIONS

J. Howard et al., "*Absolute Rate Constants for Hydrocarbon Oxidation. XI. The Reactions of Tertiary Peroxy Radicals[1,2]*", Canadian Journal of Chemistry, 1968, vol. 47, pp. 2656-2660.

J. Howard et al., "*Absolute Rate Constants for Hydrocarbon Oxidation. VIII. The Reactions of Cumylperoxy Radicals[1]*", Canadian Journal of Chemistry, 1968, vol. 46, pp. 1018-1022.

J. Howard, "*Absolute Rate Constants for Hydrocarbon Autoxidation. XXII. The Autoxidation of Some Vinyl Compounds[1]*", Canadian Journal of Chemistry, 1972, vol. 50, pp. 2298-2304.

J. Howard et al., "*Absolute Rate Constants for Hydrocarbon Autoxidation. XV. The Induced Decomposition of Some T-Hydroperoxides[1]*", Canadian Journal of Chemistry, 1969, vol. 47, pp. 3797-3801.

J. Howard et al., "*Absolute Rate Constants for Hydrocarbon Autoxidation. XIV. Termination Rate Constants for Tertiary Peroxy Radicals[1]*", Canadian Journal of Chemistry, 1969, vol. 47, pp. 3793-3795.

Y. Ishii et al., "*Recent Progress in Aerobic Oxidation of Hydrocarbons by N-Hydroxyimides*", Catalysis Today, 2006, vol. 117, pp. 105-113.

T. Iwahama et al., "*Aerobic Oxidation of Alcohols to Carbonyl Compounds Catalyzed by N-Hydroxyphthalimide (NHPI) Combined with Co (acac)$_3$*", Tetrahedron Letters, 1995, vol. 36, No. 38, pp. 6923-6926.

J. Kochi, "*Chemistry of Alkoxy Radicals: Cleavage Reactions*", Journal of the American Chemical Society, 1962, vol. 84, pp. 1193-1197.

S. Sakaguchi et al., "*Oxidation of Organic Substrates with Molecular Oxygen Catalyzed by Vanadomolybdophosphate (NPV$_6$ Mo$_6$) Combined with N-Hydroxyphthalimide (NHPI)*", Technology Reports of Kansai University, 1996, No. 38, pp. 123-131.

R. Sheldon et al., "*Organocatalytic Oxidations Mediated by Nitroxyl Radicals*", Advanced Synth. Catal., 2004, vol. 346, pp. 1051-1071.

Y. Yen, "*Phenol*", Process Economics Report No. 22B, Stanford Research Institute, 1977, pp. 113-121, 261 and 263.

\* cited by examiner

OXIDATION OF HYDROCARBONS

PRIORITY CLAIM

This application claims the benefit of PCT Application No. PCT/US2009/054000 filed Aug. 17, 2009 and U.S. provisional application Ser. No. 61/104,301 filed Oct. 10, 2008, both of which are hereby incorporated by reference in their entirety.

CROSS REFERENCE TO RELATED APPLICATION

This application is related to U.S. granted Pat. No. 7,446,232; U.S. Application No. 12/601,549, filed Jul. 11, 2008; Ser. No. 12/675,342, filed Oct. 8, 2008; Ser. No. 12/678,419, filed Oct. 8, 2008; International Patent Cooperation Treaty Application Nos. PCT/US2010/041801, filed Jul. 13, 2010; PCT/US2010/050970, filed Sept. 30, 2010 and International Patent Cooperation Treaty Application No. PCT/US2010/057753, filed Nov. 23, 2010.

FIELD

The present invention relates to a process for oxidizing hydrocarbons and, in particular, alkylaromatic hydrocarbons to produce phenol and substituted phenols.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons is used to produce phenol, a precursor in the production of polycarbonates and epoxy resins.

Oxidation of hydrocarbons can be conducted using well-known oxidizing agents, such as $KMnO_4$, $CrO_3$ and $HNO_3$. However, these oxidizing agents have the disadvantage that their use is accompanied by the production of unwanted coupling products which can pose disposal and pollution problems.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autoxidation of hydrocarbons. Thus, for example, the oxidation of cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom from a further hydrocarbon. In addition to metal salts, however, organic molecules can also act as free-radical initiators.

However, it is a disadvantage of these processes that the selectivity decreases very greatly with increasing conversion and therefore the processes must be operated at a very low level of conversion. Thus, for example, the oxidation of cyclohexane to cyclohexanol/cyclohexanone is carried out at a conversion of 10 to 12% so that the selectivity is 80 to 85% ("Industrielle Organische Chemie" [Industrial Organic Chemistry] 1994, 261, VCH-Verlag, D-69451 Weinheim).

An alternative to metal salt catalysts is the use of organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a cyclic imide catalyst, typically a N-hydroxycarbodiimide catalyst, such as N-hydroxyphthalimide (NHPI). The process is conducted at a temperature between 0° C. and 500° C. and a pressure between atmospheric and 100 bar (100 and 10,000 kPa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene and sec-butylbenzene.

U.S. Pat. No. 7,038,089 discloses a process for preparing a hydroperoxide from a hydrocarbon selected from a group consisting of primary hydrocarbons, secondary hydrocarbons and mixtures thereof corresponding to said hydroperoxide which comprises conducting the oxidation of said hydrocarbon at a temperature in the range between 130 and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, ethylbenzene, diisopropylbenzene, cyclohexylbenzene, tetrahydronaphthalene (tetraline), indane, etc.), and the like. The amount of the cyclic imide compound used may be from 0.0001 to 1%, preferably from 0.0005 to 0.5 wt %, based on the reaction mixture, whereas the amount of the alkali metal compound may be from 0.000005 to 0.01%, preferably from 0.00001 to 0.005 wt % based on the reaction mixture However, while cyclic imides have shown activity and selectivity for the oxidation of hydrocarbons to products, such as hydroperoxides, they suffer from the problem that they can be hydrolyzed to non-catalytic species in the presence of the water and organic acids that tend to be generated as common by-products of the oxidation process. Moreover, under oxidation conditions, carbon-carbon bond scission reactions can generate alkyl radicals that can react with oxygen to terminate radical chain propagation and produce undesirable organic acids, such as acetic acid. For example, acetic acid not only facilitates hydrolysis of N-hydroxycarbodiimides, but also catalyzes the exothermic decomposition of hydroperoxide products, which can result in dangerous temperature excursions as well as producing oxidation poisons.

In our co-pending U.S. Patent Application No. 60/984,271, filed Oct. 31, 2007, the entire contents of which are incorporated herein by reference, we have described a process for oxidizing hydrocarbons in the presence of a cyclic imide catalyst, in which the problem of catalyst decomposition is alleviated by controlling the reaction conditions so as to maintain the concentration of water and organic acids in the reaction medium below 50 ppm. This is achieved by operating the process at low pressure and low oxygen concentration and by passing a stripping gas through the reaction medium to strip water and organic acids from the reaction products as they are formed.

In accordance with the present invention, an alternative method of alleviating the problem of catalyst decomposition is proposed in which a slip stream of the contents of the oxidation reaction medium is removed from the oxidation reactor and is then stripped of water and organic acids before being returned to the reactor. Typically, this is achieved by reducing the pressure of the reaction medium portion to flash off the water and organic acid impurities. In this way, the overall concentration of water and organic acids can be controlled even when the oxidation reaction is run at relatively high pressures so as to increase the oxidation rate.

SUMMARY

In one aspect, the present invention resides in a process for oxidizing a hydrocarbon to the corresponding hydroperoxide, alcohol, ketone, carboxylic acid or dicarboxylic acid, the process comprising;
(a) contacting a reaction medium comprising a hydrocarbon with an oxygen-containing gas in a reaction zone and in the presence of a catalyst comprising a cyclic imide of the general formula (I):

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N, and $CR^3$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^3$ can be any of the entities (radicals, groups, or atoms) listed for $R^1$;
(b) removing a portion of said reaction medium from said reaction zone, said reaction medium portion containing water and organic acids;
(c) stripping at least part of water and organic acids from said reaction medium portion; and then
(d) returning at least part of the stripped reaction medium portion to said reaction zone.

In one embodiment, the stripping (c) includes reducing the pressure of said reaction medium portion to facilitate flashing of water and organic acids therefrom.

In another embodiment, the stripping (c) includes passing a stripping gas, conveniently air, through said reaction medium portion.

Conveniently, the stripping (c) is conducted in a plurality of stages.

Conveniently, the process further comprises drying at least part of the stripped reaction medium before said returning (d).

Conveniently, said contacting (a) is conducted at a temperature of about 20° C. to about 150° C., such as at a temperature of about 70° C. to about 130° C.

Conveniently, said contacting (a) is conducted at a pressure of about 100 kPa to about 7000 kPa, such as at a pressure of greater than 500 kPa to about 5000 kPa.

In one embodiment, said hydrocarbon is an alkane or cycloalkane, such as isobutane or cyclohexane.

In another embodiment, said hydrocarbon is an alkylaromatic compound of general formula (II):

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, and said contacting produces a hydroperoxide of general formula (IV):

(IV)

in which $R^4$, $R^5$ and $R^6$ have the same meaning as in formula (II).

Conveniently, said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

Conveniently, the process further includes converting the hydroperoxide of formula (IV) into phenol and an aldehyde or ketone of the general formula $R^4COCH_2R^5$ (V), in which $R^4$ and $R^5$ have the same meaning as in formula (I).

DETAILED DESCRIPTION OF THE EMBODIMENTS

The terms "group", "radical", and "substituent" are used interchangeably in this document. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical.

As used herein, the new numbering scheme for the Periodic Table Groups is employed as disclosed in Chemical and Engineering News, 63(5), 27 (1985).

The present invention provides a process for oxidizing a hydrocarbon to the corresponding hydroperoxide, alcohol, ketone, carboxylic acid or dicarboxylic acid. The process comprises contacting a reaction medium comprising a hydrocarbon with an oxygen-containing gas in a reaction zone and in the presence of a catalyst comprising a cyclic imide of the general formula (I):

(I)

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I, provided that $R^1$ and $R^2$ can be linked to one another via a covalent bond; each of $Q^1$ and $Q^2$ is independently selected from C, CH, N, and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3; and $R^3$ can be any of the entities (radicals, groups, or atoms) listed for $R^1$.

Under the conditions in the reaction zone, the hydrocarbon is oxidized to the desired product, such as a hydroperoxide, but in addition water and organic acids tend to be generated as by-products. Since water and organic acids can hydrolyze the cyclic imide catalyst, during the contacting a portion of the reaction medium is removed from the reaction zone and at least part of the water and organic acids contained therein is stripped from reaction medium portion. The stripped reaction medium portion can then be returned to the reaction zone. In this way, the amount of water and organic acids in the reaction medium can be maintained at relatively low levels, typically below 50 ppm, so as to minimize loss of the cyclic imide.

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexanol and cyclohexanone and the selective oxidation of alkylaromatic compounds of the general formula (II) to the corresponding hydroperoxides:

(II)

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In an embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-penty-lbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^4$ and $R^5$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (II) is sec-butylbenzene and is produced by alkylating benzene with at least $C_4$ alkylating agent under alkylation conditions and in the presence of a heterogeneous catalyst, such as zeolite beta or more preferably at least one molecular sieve of the MCM-22 family (as defined below). The alkylation conditions conveniently include a temperature of from about 60° C. to about 260° C., for example between about 100° C. and about 200° C., a pressure of 7000 kPa or less, for example from about 1000 to about 3500 kPa, and a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product of remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C., a pressure of about 100 to about 7000 kPa, a benzene to hydrogen molar ratio of about 0.01 to about 100 and a WHSV of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is effected by contacting the hydrocarbon substrate with an oxygen-containing gas in a reaction zone and in the presence of a catalyst comprising a cyclic imide of the general formula (I):

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I provided that $R^1$ and $R^2$ can be linked to one another via a covalent bond; each of $Q^1$ and $Q^2$ is independently selected from C, CH, N, and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3, and $R^3$ can be any of the entities (radicals, groups, or atoms) listed for $R^1$. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide (NHPI) and is preferably present in the reaction zone in an amount between about 0.0001 wt % and about 5 wt %, such as between about 0.1 wt % and about 1 wt %, of the hydrocarbon substrate.

The oxidation of the hydrocarbon substrate is typically conducted at a temperature between about 20° C. and about 300° C., more particularly between about 50° C. and about 130° C. and/or a pressure between about 100 kPa and about 7000 kPa, more particularly greater than 500 kPa to about 5000 kPa and/or an oxygen concentration from 0.1 to 100% volume %, generally from about 2 to about 10 volume %, oxygen in the oxygen-containing gas. These conditions are effective not only to affect the desired oxidation of the substrate but also to generate significant quantities of both water and organic acids (e.g., acetic and/or formic acid) in the reaction medium. Thus, to reduce the loss of NHPI through hydrolysis, a slip stream of the oxidation reaction medium is removed, either continuously or intermittently, from the reaction zone and is then stripped of volatile components, such as water and acetic and/or formic acid. The stripping is conveniently effected by reducing the pressure of the slip stream to facilitate flashing of the volatile components. Additionally, or alternatively, a stripping gas can be passed through the slip stream to aid in removal of the volatile components. Suitable stripping gases include the oxygen-containing gas used for the oxidation step, as well as gases inert to the reaction medium and the cyclic imide catalyst, such as helium and argon. Conveniently, some or all of the flue gas from the oxidation reactor may be used as the stripping gas. This flue gas is mainly oxygen-depleted air and comprises the gas exiting the reaction zone after the contacting of the oxygen-containing gas and the hydrocarbon. The flue gas may be treated to remove water and/or acids. Preferably the flue gas is passed through a chilled condenser and/or a sorbent bed to remove entrained water and/or acids prior to contacting the slip stream.

Typically the stripping is effected as a multi-stage process, for example by lowering the pressure of the slip stream and then passing a stripping gas through the slip steam.

After stripping of the slip stream of some or all of water and organic acid impurities, the slip stream is returned to the reaction zone, normally after drying the slip stream using, for example, a guard bed. In this way, it is possible to maintain the amount of water and organic acids in the reaction medium at relatively low levels, typically below 50 ppm, so as to minimize loss of the NHPI by hydrolysis.

An additional advantage of the outboard stripping process described above is that light hydroperoxide (e.g., ethyl or methyl hydroperoxide), light ketones (e.g., methyl ethyl ketone), light aldehydes (e.g., acetaldehyde) and light alcohols (e.g., ethanol) are also removed from slip stream during the stripping process. Light hydroperoxides are hazardous and pose a safety concern if their concentration in the reaction medium becomes too high. Also, light hydroperoxides, alcohols, aldehydes and ketones are precursors for the formation of organic acids and water so that removing these species from the oxidation medium improves the oxidation reaction rate and selectivity and the stability of the cyclic imide catalyst.

Figure 1:
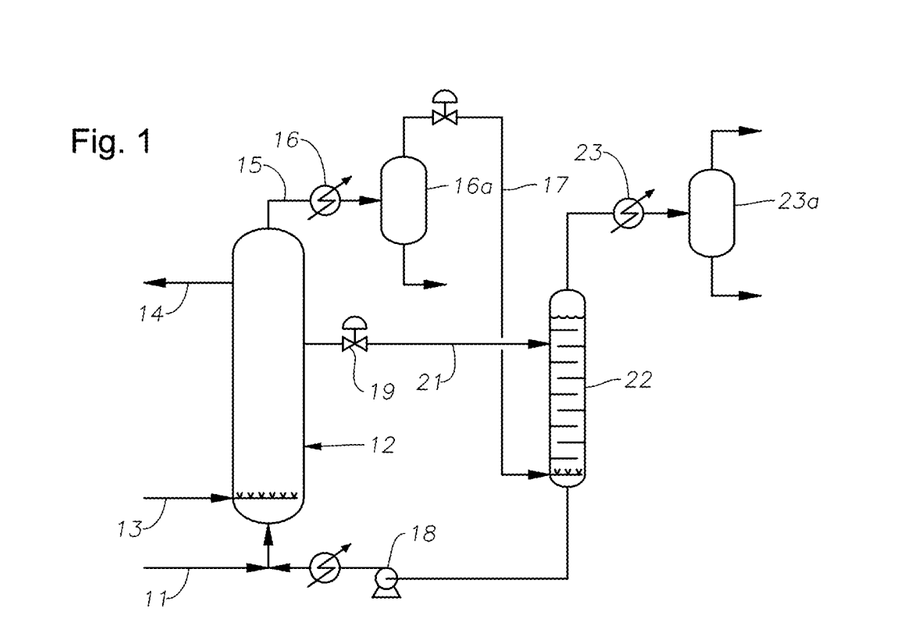
FIG. 1 is a flow diagram of a hydrocarbon oxidation process according to a first embodiment of the invention.
Figure 2:
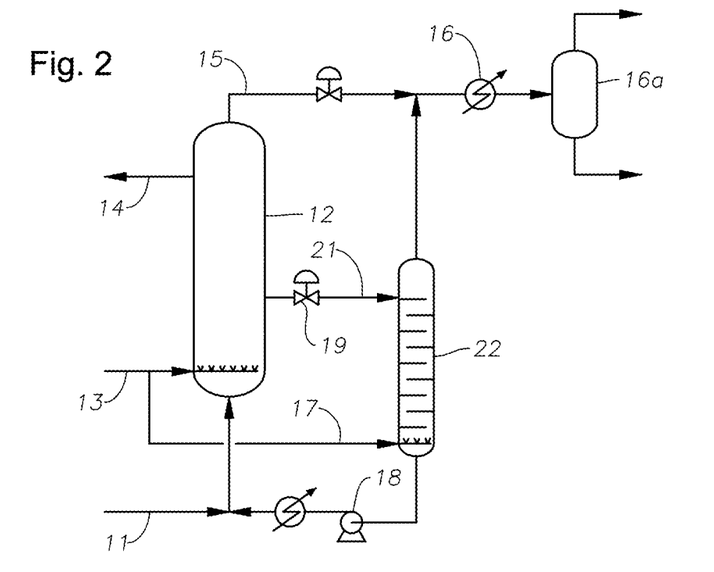
FIG. 2 is a flow diagram of a hydrocarbon oxidation process according to a second embodiment of the invention.

Referring now to FIGS. 1 and 2 of the accompanying drawings, a first embodiment of the present oxidation process is shown in FIG. 1, in which a hydrocarbon feed 11 having a cyclic imide catalyst dissolved therein is passed through a vertically disposed oxidation reactor 12 concurrent with a compressed air stream 13. The feed 11 and stream 13 are introduced into the reactor 12 near its base and a liquid oxidized effluent stream 14 and a flue gas stream 15 are withdrawn from the reactor 12 at or near the top of the reactor. The oxidized effluent stream 14 is recovered or passed to the next stage of the process, while the flue gas stream 15 is cooled and then passed to a condenser 16 and a knock-out vessel 16a for the removal of entrained water, organic acids and unreacted hydrocarbon by way of condensed stream 17a. The gaseous effluent from the condenser 16 is a stripping gas 17 composed of oxygen-depleted air.

Continuously removed from the reactor 12 under the control of a valve 19 is a slip stream 21 of the oxidation reaction medium. The slip stream 21 is passed to the top of a vertically disposed stripping column 22, while the stripping gas 17 is injected into the bottom of the column 22. Thus as the reaction medium flows down through the column 22, the stripping gas 17 passes countercurrent up through the reaction medium to remove water and organic acids produced during the oxidation process. The purified reaction medium is removed from the base of the stripping column 22 and returned by the pump 18 to the reactor 12, while the used stripping gas is removed from the top of the column 22 and passed through a further condenser 23 for removal of water and organic components prior to venting to atmosphere.

A second embodiment of the present oxidation process is shown in FIG. 2 and differs from the process shown in FIG. 1 in that a portion of the compressed air stream 13 is used as the stripping gas 17 fed to the column 22. In addition, a single condenser 16 is used to remove the water and organic acids entrained in the flue gas stream 15 and the used stripping gas before both streams are vented to atmosphere.

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

For example, when the hydrocarbon substrate is isobutane, the oxidation product comprises tertiary butyl hydroperoxide (which is useful as an oxidation reagent and in the production of propylene oxide) and tertiary butanol (which is useful as a gasoline additive).

When the hydrocarbon substrate is cyclohexane, the oxidation product comprises cyclohexyl hydroperoxide, cyclohexanol and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of Nylon 6, 6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (II), the product of the oxidation reaction includes a hydroperoxide of general formula (IV):

(IV)

in which $R^4$, $R^5$ and $R^6$ have the same meaning as in formula (II). Preferably, the hydroperoxide is sec-butylbenzene hydroperoxide or cyclohexylbenzene hydroperoxide. This hydroperoxide can then be converted by acid cleavage to phenol or a substituted phenol and an aldehyde or ketone of the general formula $R^4COCH_2R^5$ (V), in which $R^4$ and $R^5$ have the same meaning as in formula (II).

In one embodiment, the alkylaromatic compound that is oxidized is cyclohexylbenzene, the oxidation product is cyclohexylbenzene hydroperoxide, and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to hydrogenation in order to convert it to phenol. Such hydrogenation may be performed, for example, over a catalyst such as platinum, nickel or palladium.

The cleavage reaction is conveniently affected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 1000 hr$^{-1}$, preferably about 1 to about 50 hr$^{-1}$. The hydroperoxide is preferably diluted in an organic solvent inert to the cleavage reaction, such as methyl ethyl ketone, phenol, cyclohexylbenzene, cyclohexanone and sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the following non-limiting Examples and FIGS. 3 to 6 of the accompanying drawings.

EXAMPLE 1

150 gm of sec-butylbenzene (SBB) supplied by TCI America and 0.16 gm (0.11 wt %) of N-hydroxyphthalimide (NHPI) were weighed into a Parr reactor fitted with a stirrer, thermocouple, gas inlet, sampling port and a condenser containing a DeanStark trap for water removal. The reactor and contents were stirred at 700 rpm and sparged with nitrogen at a flow rate of 250 cc/minute for 5 minutes. The reactor was then pressurized with nitrogen to 100 psig (790 kPa) while maintained under a nitrogen sparge and was then heated to 125° C. When the reaction temperature was reached, the gas was switched from nitrogen to air and the reactor was sparged with air at 250 cc/minute for 4 hours. Samples were taken hourly and the NHPI, acetic acid and reaction concentrations of each sample were measured by gas chromatography for conversion and selectivity and HPLC (High pressure liquid chromatography) for NHPI concentration measurements. For water analysis Karl Fischer analysis was used. After 4 hours, the gas was switched back to nitrogen and the heat was turned off. When the reactor had cooled, it was depressurized and the contents removed.

Figure 3:
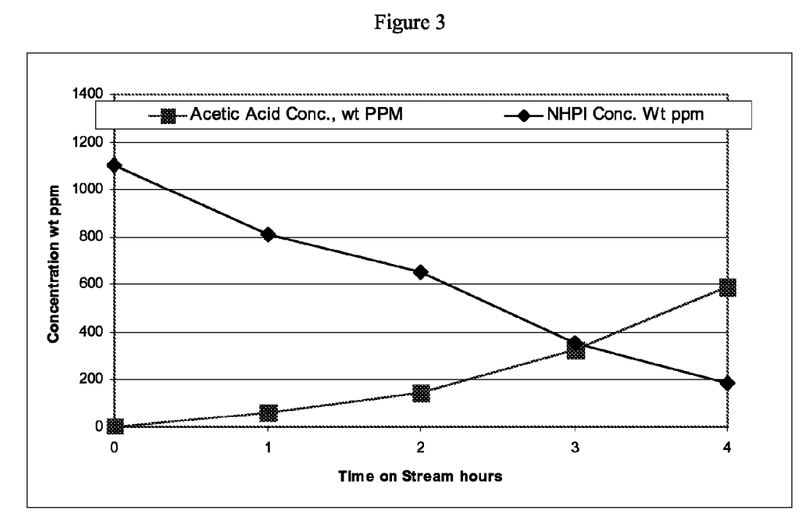
FIG. 3 is a graph plotting acetic acid and NHPI concentrations against time on stream in the oxidation of sec-butylbenzene (SBB) in the presence of 0.11 wt % NHPI at 790 kPa (100 psig) according to the process of Example 1.

The results are shown in FIG. 3, from which it will be seen that the NHPI concentration dropped from 1100 ppm at the beginning of the test to 185 ppm over 4 hours, during which time the acetic acid concentration built up from zero to about 600 ppm.

EXAMPLE 2

Figure 4:
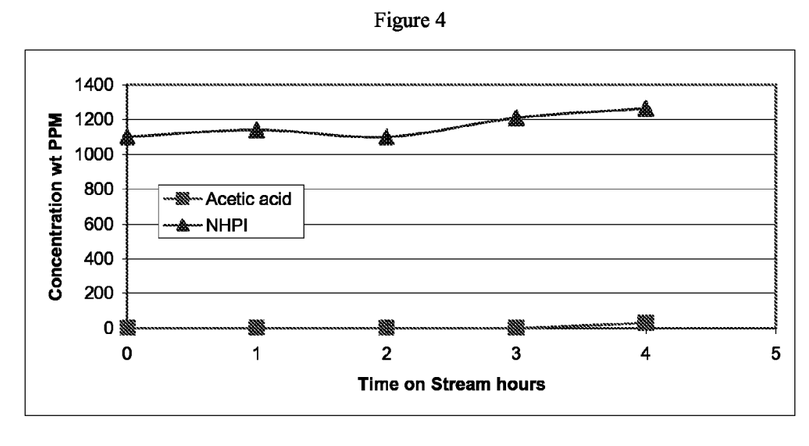
FIG. 4 is a graph plotting acetic acid and NHPI concentrations against time on stream in the oxidation of SBB in the presence of 0.11 wt % NHPI at 100 kPa (atmospheric pressure) according to the process of Example 2.

The process of Example 1 was repeated, but with the test being run at atmospheric pressure (100 kPa) and the results are shown in FIG. 4. It will be seen that, at atmospheric pressure (100 kPa), acetic acid and other light acids were formed at very low concentration and were completely removed from the reaction mixture, making them unavailable to catalyze the hydrolysis of the NHPI. In fact for the first 3 hours of the test, the acetic acid level was below the detection limits of the gas chromatographic analysis, rising to only 30 ppm (in contrast with the 600 ppm obtained in Example 1), by the end of the 4 hour run time. In addition to stripping acetic acid from the reaction mixture, at low pressure the air flowing through the reaction mixture strips out the majority of the water also generated as a by-product of the oxidation process.

The NHPI concentration during the test of Example 2 is also shown in FIG. 4, from which it will be seen that the concentration of NHPI started out at 1100 ppm and drifted up slowly during the test as other volatile components were stripped from the reaction mixture. Thus, at low pressure, with most of the acetic acid and water removed, the NHPI catalyst in the reaction vessel was protected from hydrolysis and remained close to its starting concentration and available for the oxidation reaction.

Figure 5:
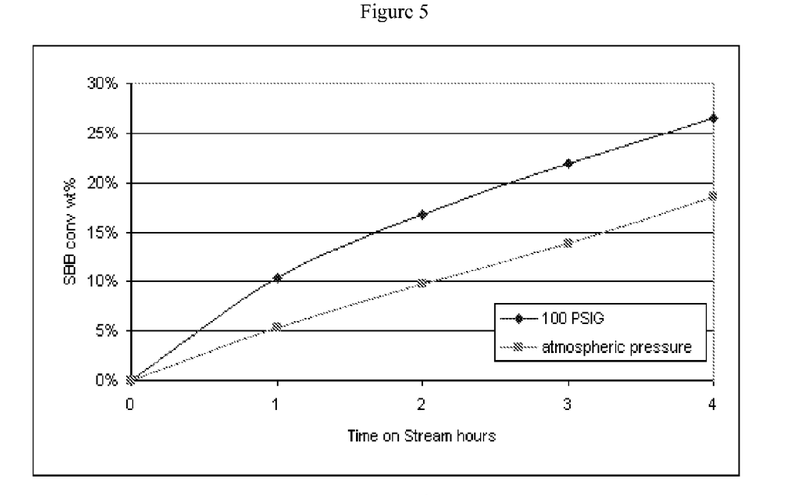
FIG. 5 is a graph comparing the SBB conversion against time on stream for the processes of Examples 1 and 2.
Figure 6:
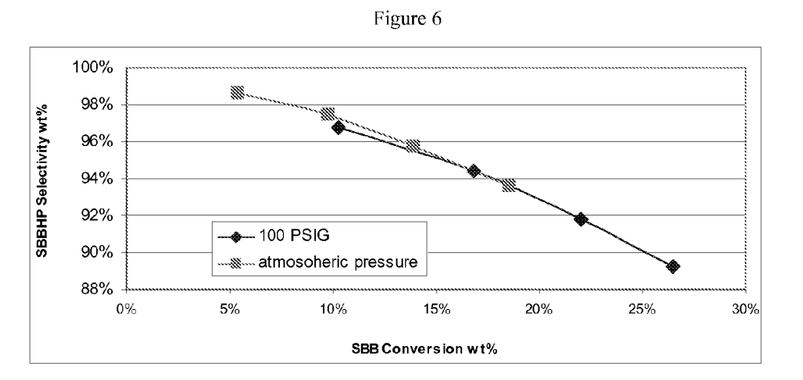
FIG. 6 is a graph comparing the sec-butylbenzene hydroperoxide (SBBHP) selectivity against SBB conversion for the processes of Examples 1 and 2.

The SBB conversion and the selectivity to sec-butylbenzene hydroperoxide (SBBHP) for Examples 1 and 2 are compared in FIGS. 5 and 6. It will be seen from FIG. 5 that the SBB conversion was adversely affected by the lower pressure used in Example 2, decreasing from 26 wt % after 4 hours in Example 1 to only 18 wt % in Example 2, a loss in conversion of about 30%. As can be seen from FIG. 6, the SBBHP selectivity versus SBB conversion response was very similar at both 100 psig and atmospheric pressure, indicating that the SBBHP selectivity was set by the SBB conversion selected and was not a function of pressure at these reaction conditions.

Based on the above results, it would appear to be preferable to operate the oxidation at higher pressures, especially if this can be achieved without excessive loss of NHPI by hydrolysis. The outboard stripping process proposed herein provides such a method of maintaining the hydrolytic agents, water and acetic acid, at low levels while allowing the overall oxidation process to be run at high pressure.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A process for oxidizing a hydrocarbon to the corresponding hydroperoxide, alcohol, ketone, carboxylic acid or dicarboxylic acid, the process comprising
(a) contacting a reaction medium comprising a hydrocarbon with an oxygen-containing gas in a reaction zone and in the presence of a catalyst comprising a cyclic imide of the general formula (I):

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N, and $CR^3$;

each of X and Z is independently selected from C, S, CH$_2$, N, P and elements of Group 4 of the Periodic Table;
Y is O or OH;
k is 0, 1, or 2;
l is 0, 1, or 2;
m is 1 to 3; and
R$^3$ can be any of the entities (radicals, groups, or atoms) listed for R$^1$;
(b) removing a portion of said reaction medium from said reaction zone, said reaction medium portion containing water and organic acids;
(c) stripping at least part of water and organic acids from said reaction medium portion; and then
(d) returning at least part of said reaction medium portion to said reaction zone.

2. The process of claim 1, wherein the stripping (c) includes reducing the pressure of said reaction medium portion to facilitate flashing of water and organic acids therefrom.

3. The process of claim 1, wherein the stripping (c) includes passing a stripping gas through said reaction medium portion.

4. The process of claim 3, wherein said stripping gas comprises air.

5. The process of claim 3, wherein said stripping gas comprises at least a portion of flue gas exiting the reaction zone.

6. The process of claim 5, wherein the at least portion of flue gas exiting the reaction zone is treated to remove water and/or acids therefrom before being used as said stripping gas.

7. The process of claim 1, wherein the stripping (c) is conducted in a plurality of stages.

8. The process of claim 1, and further comprising drying at least part of the stripped reaction medium before said returning (d).

9. The process of claim 1, wherein said cyclic imide obeys the general formula (III):

(III)

wherein each of R$^7$, R$^8$, R$^9$, and R$^{10}$ is independently selected from hydrocarbyl and substituted hydrocarbyl radicals having 1 to 20 carbon atoms, or from the groups SO$_3$H, NH$_2$, OH, and NO$_2$ or from the atoms H, F, Cl, Br, and I;
each of X and Z is independently selected from C, S, CH$_2$, N, P and elements of Group 4 of the Periodic Table;
Y is O or OH;
k is 0, 1, or 2; and
l is 0, 1, or 2.

10. The process of claim 1, wherein said cyclic imide comprises N-hydroxyphthalimide.

11. The process of claim 1, wherein said contacting (a) is conducted at a temperature of about 20° C. to about 150° C.

12. The process of claim 1, wherein said contacting (a) is conducted at a pressure of about 100 kPa to about 7000 kPa.

13. The process of claim 1, wherein said hydrocarbon comprises an alkane or cycloalkane.

14. The process of claim 1, wherein said hydrocarbon comprises an alkylaromatic compound of general formula (II):

(II)

wherein R$^4$ and R$^5$ each independently represents hydrogen or an alkyl group having from 1 to 4 carbon atoms, provided that R$^4$ and R$^5$ may be joined to form a cyclic group having from 4 to 10 carbon atoms, said cyclic group being optionally substituted, and R$^6$ represents hydrogen, one or more alkyl groups having from 1 to 4 carbon atoms or a cyclohexyl group, and said contacting produces a hydroperoxide of general formula (IV):

(IV)

in which R$^4$, R$^5$ and R$^6$ have the same meaning as in formula (II).

15. The process of claim 14, wherein said alkylaromatic compound of general formula (II) is selected from ethyl benzene, cumene, sec-butylbenzene, sec-pentylbenzene, p-methyl-sec-butylbenzene, 1, 4-diphenylcyclohexane, sec-hexylbenzene, and cyclohexylbenzene.

16. The process of claim 14, and further including converting the hydroperoxide of formula (IV) into phenol and an aldehyde or ketone of the general formula R$^4$COCH$_2$R$^5$ (V), in which R$^4$ and R$^5$ have the same meaning as in formula (I).

17. The process of claim 16, wherein said hydroperoxide is cyclohexylbenzene hydroperoxide and said ketone is cyclohexanone which process further comprises dehydrogenating the cyclohexanone to produce further phenol.

18. The process of claim 1, wherein said contacting (a) is conducted at a pressure of about 500 kPa to about 5000 kPa.

* * * * *